(12) United States Patent
Semanoukian et al.

(10) Patent No.: US 11,501,624 B2
(45) Date of Patent: *Nov. 15, 2022

(54) APPARATUS, SYSTEM AND METHOD FOR A PORTABLE PERSONAL AIR QUALITY MONITOR

(71) Applicant: JABIL INC., St. Petersburg, FL (US)

(72) Inventors: Edouard Semanoukian, San Jose, CA (US); Jason Petker, St. Petersburg, FL (US)

(73) Assignee: JABIL INC., St. Petersburg, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/119,860

(22) Filed: Dec. 11, 2020

(65) Prior Publication Data

US 2021/0142645 A1  May 13, 2021

Related U.S. Application Data

(63) Continuation of application No. 16/159,367, filed on Oct. 12, 2018, now abandoned, which is a continuation of application No. 15/268,310, filed on Sep. 16, 2016, now Pat. No. 10,467,880.

(51) Int. Cl.
*G08B 21/12* (2006.01)
*G01N 33/00* (2006.01)

(52) U.S. Cl.
CPC ......... *G08B 21/12* (2013.01); *G01N 33/0031* (2013.01); *G01N 33/0062* (2013.01)

(58) Field of Classification Search
None
See application file for complete search history.

(56) References Cited

U.S. PATENT DOCUMENTS

| | | | | |
|---|---|---|---|---|
| 6,693,546 | B2* | 2/2004 | Skardon | G16H 40/63 340/627 |
| 2010/0217099 | A1* | 8/2010 | LeBoeuf | A61B 5/4812 600/301 |
| 2013/0035869 | A1* | 2/2013 | Minges | G01N 33/0004 702/24 |
| 2014/0277624 | A1* | 9/2014 | Pariseau | G05B 11/01 700/90 |

* cited by examiner

*Primary Examiner* — Thomas S Mccormack
(74) *Attorney, Agent, or Firm* — Thomas J. McWilliams; Barnes & Thornburg LLP

(57) ABSTRACT

Apparatuses, systems and methods of providing a personal air quality monitor. The personal air quality monitor may include a housing suitable for physical association with a person; an air inlet capable of providing air flow from an environment outside the housing to a chamber within the housing; a plurality of sensor resident within the chamber, suitable for receiving the airflow and measuring air quality factors associated with the airflow; and a communication system suitable for processing the air quality factor measurements and communicating the processed air quality factor measurements to a user interface cognizable to the person.

14 Claims, 10 Drawing Sheets

APPARATUS, SYSTEM AND METHOD FOR A PORTABLE PERSONAL AIR QUALITY MONITOR

CROSS-REFERENCE TO RELATED APPLICATIONS

The present application is a continuation application of U.S. Non-Provisional application Ser. No. 16/159,367, filed Oct. 12, 2018, entitled "Apparatus, System and Method for a Portable Personal Air Quality Monitor", which is a continuation application of Non-Provisional application Ser. No. 15/268,310, filed Sep. 16, 2016, entitled "Apparatus, System and Method for a Portable Personal Air Quality Monitor," which is incorporated by reference in its entirety herein.

BACKGROUND

Field of the Disclosure

The disclosure relates to air quality, and, more particularly, relates to an apparatus, system and method for a portable, personal air quality monitor.

Description of the Background

The term "air quality" indicates the state of the air in a given environment. Good air quality typically refers to "clean," i.e., unpolluted, air. Clean air is essential for the health of humans, wildlife, vegetation, water and soil. Poor air quality may be the result of a number of factors, including emissions from various sources, including natural and human-caused emissions. For example, automobile, fossil fuel burning and livestock emissions can all have a significant effect on air quality. Poor air quality occurs when pollutants reach sufficiently significant concentrations to endanger or adversely impact human health or the environment.

Good outdoor air quality is vital to the well-being of humans and the natural environment. On average, a person inhales about 14,000 liters of air daily, and so the presence of significant pollutants in the inhaled air will have a significant adverse effect on health, either acutely or over time. Needless to say, those with pre-existing respiratory and heart conditions, diabetes, the young, and the elderly are particularly vulnerable.

Studies have repeatedly shown that poor air quality also adversely affects the natural environment. For example, ecological damage may occur when air pollutants come into direct contact with vegetation, or when inhaled by animals inhale. Pollutants may also settle out of the air onto land and water. From the soil, pollutants may wash into waterways, or be taken up by plants and animals. Further, some pollutants have a warming effect on the atmosphere.

The detrimental effects of poor air quality on human health and the environment, in turn, have negative economic impacts. Significant costs, for example, for hospitalization and medical treatment, premature death, and lost work time, may be incurred due to poor air quality. Moreover, damage to soil, vegetation, and waterways may reduce agricultural productivity, and, in urban areas, air pollution can be costly by, for example, disrupting transport or travel, or by corroding equipment or buildings.

Ambient air quality refers to the quality of outdoor air. It is preferably measured near ground level, away from direct sources of pollution and at the height relevant to breathing of the air by humans. Accordingly, outdoor air quality stations are typically placed in various geographical locations at ground level, such as by government agencies, in order to monitor and collect air quality data.

Air quality may be degraded when unwanted chemicals, substances or materials enter the air in large enough quantities to have detrimental effect, such as on the health of people, plants, animals, buildings, equipment, and/or the environment. This is termed "air pollution," and the substances detrimental to the air are termed "air pollutants." The extent of the pollution of the air depends on the amount of pollutants, the rate at which the pollutants are released from various sources, and how quickly the pollutants disperse, or conversely, how long the pollutants are held or trapped in an area.

More particularly, air pollutants may occur as gases, or tiny solid particles, such as dust, mold, smoke, soot, cigarette smoke, mites, dander, formaldehyde, volatile organic compounds (VOCs), or radon gas. Pollutants may be emitted from natural sources, such as volcanoes, but many come from human and animal activity.

In areas with good airflow, pollutants will mix with the air and quickly disperse. However, when pollutants are trapped in an area, pollutant concentrations may increase rapidly. Trapping of pollution may occur, for example, when weather conditions (e.g., light winds and/or a temperature inversion), and/or nearby terrain (e.g., mountains) limit the movement of pollutants away from an area, thus resulting in poor air quality.

Air quality may be measured in one of two ways: either through continuous or noncontinuous monitoring. For continuous monitoring, air is constantly measured, and the data on air quality is continuously generated and stored. For noncontinuous monitoring, air may be monitored only periodically, or contaminants may be collected on a filter or in a canister over a period of time. In noncontinuous monitoring, data is only generated intermittently correspondent to the measurement period.

Therefore, the need exists for an air quality monitor that provides for improved monitoring of air quality in locations most important to particular individuals and to the environment, continuously or noncontinuously.

SUMMARY

The disclosed apparatuses, systems and methods provide at least a personal air quality monitor. The personal air quality monitor may include a housing suitable for physical association with a person; an air inlet capable of providing air flow from an environment outside the housing to a chamber within the housing; a plurality of sensor resident within the chamber, suitable for receiving the airflow and measuring air quality factors associated with the airflow; and a communication system suitable for processing the air quality factor measurements and communicating the processed air quality factor measurements to a user interface cognizable to the person.

More particularly, the disclosed method of monitoring air quality may include providing, through an air access point, air to one or more air quality factor sensors of a personal, portable air quality monitor; reading an air quality factor indicated by each of the one or more air quality factor sensors; processing the data from the one or more sensors into at least one indication of air quality; and displaying the at least one indication of air quality to a person associated with the personal, portable air quality monitor.

Thus, the disclosed embodiments provide an air quality monitor that provides for improved monitoring of air quality in locations most important to particular individuals and to the environment, continuously or noncontinuously.

BRIEF DESCRIPTION OF THE FIGURES

The foregoing summary, as well as the following detailed description, will be better understood when read in conjunction with the appended drawings. For the purpose of illustrating the invention, there are shown in the drawings embodiments which are exemplary. It should thus be understood that the disclosure is not limited to the precise arrangements and instrumentalities shown. In the drawings, like numerals represent like elements.

DETAILED DESCRIPTION

Figure 1A:
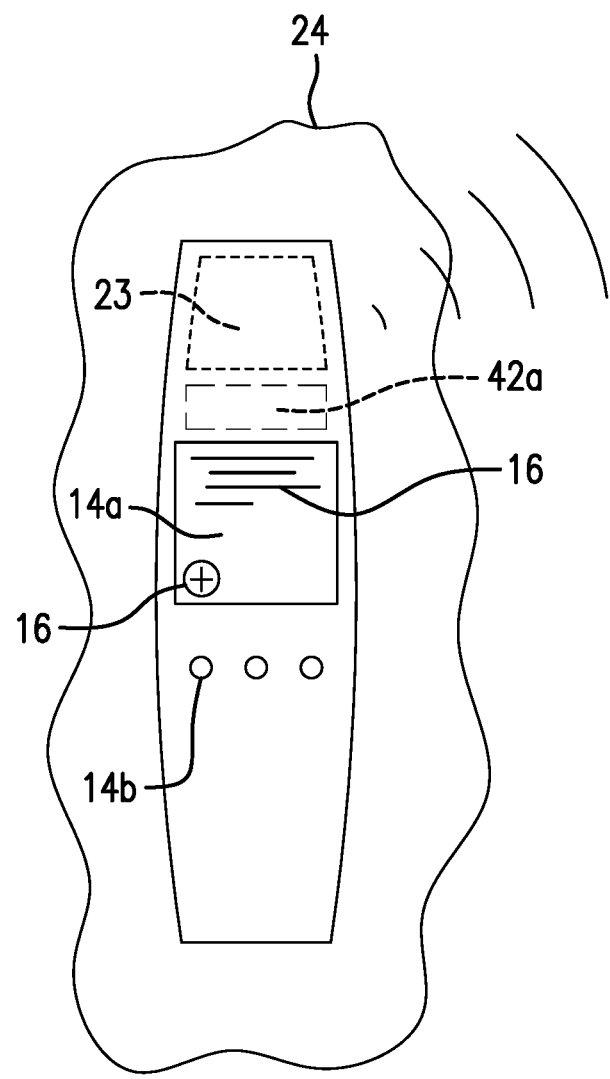
FIG. 1A is a diagram illustrating an embodiment of a personal, portable air quality monitor.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that embodiments may be embodied in different forms. As such, the embodiments detailed herein should not be construed to limit the scope of the disclosure. As referenced above, in some embodiments, well-known processes, well-known device structures, and well-known technologies may not be described in detail.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the embodiments.

In light of the aforementioned effects of negative, or poor, air quality, it is vital to the public health, to environmental well-being, and to the success of business and government, and it is particularly important for: the elderly, the young, and those in ill-health; livestock and food sources; the profitability of industry; the support of governments; and indeed to entire countries and the world, that acceptable levels of air quality be maintained. Although air quality monitoring may be important for both indoor, such as in offices, homes, airports, or gyms, and outdoor air quality, the importance of monitoring may be of particular importance in outdoor environments for a number of reasons, including that outdoor environments are shared by all of the foregoing, and that the air circulated in indoor environments is generally air initially obtained from the outdoor environment.

It has been estimated that roughly half of the world's population lives in an urban environment and suffers from some significant level of air pollution. Further, it has been estimated that some 896,000,000 persons of the world population suffer from some level of physical distress that is due to or exacerbated by air pollution. Such persons include sufferers of allergies, asthma, and COPD. It has also been estimated that approximately 50,000,000 users regularly employ fitness bands or activity trackers.

The disclosed embodiments are very relevant to all of the aforementioned persons. This is due, in part, to the ability of the disclosed personal, portable air quality monitor, system, and method to monitor for myriad air quality factors, such as carbon monoxide, carbon dioxide, nitrogen dioxide, sulfur dioxide, ground ozone, particulate pollution, lead, UV, pollen, and so on, in-situ for the user. These air quality factors are highly significant to urbanites, those suffering physical distress due to air quality, and fitness and activity enthusiasts, by way of non-limiting example.

The embodiments allow for air quality monitoring in a more relevant manner to the user than has historically been the case, i.e., the embodiments provide for improved air quality monitoring over the known, infrequently-placed government sensors. It is, of course, the case that optimal monitoring of air quality at locations where humans congregate is not accomplished by associating air quality monitoring with discrete, government-placed outdoor sensors, but rather is accomplished by associating air quality monitoring with the people, in-situ, in each environment on whose behalf the air quality should be monitored. Therefore, the disclosure provides air quality monitoring capabilities for association with individuals, and individual environments of those individuals, as the individuals move about, such that any current environment in which an individual finds herself maybe monitored. That is, if the user of the disclosed individual air quality monitor is inside an office, at a restaurant, in a park walking a dog, at a farm, inside an airplane, at a sporting event, or the like, the air quality for the air then-being consumed by that individual may be uniquely monitored in the immediate vicinity of that individual.

Moreover, the capability to independently monitor air quality may allow for the providing of alerts or notifications to the user associated with the individual air quality monitor, and in addition may allow for sharing of the data incurred by that individual's air quality monitor, such that users may additionally monitor environments in which those users are currently not present. That is, the air quality data, and/or any alerts or notifications associated with that data, may not only be made available to the user of the monitor, but may additionally be shared, such as via upload to a cloud community associated with a Web-based thin client, a desktop or mobile app, or the like, such that other users or non-users of the monitors may assess air quality in nearly any environment, whether or not those individuals are then-present in that environment. Alerts may be presented, for example: visually, such as on simple or complex display; audibly, such as by one or more tones indicating one or more aspects of air quality; tactily, such as via one or more types of vibration indicating one or more aspects of air quality; on device or off device, such as on a smartphone proximate to the device; or via any other known manner.

The afore-discussed capabilities may allow for heretofore unknown proactivity in: individual decisions for a healthier lifestyle; local and regional decisions to improve air quality; and globally addressing environmental and atmospheric issues. By way of example, not only will the monitor allow the user of the monitor, and any individuals with whom the monitor's data is shared, to avoid exposure or prolonged exposure to poor air quality environments, but additionally the disclosed embodiments may allow for an improved assessment of individuals, businesses, or locations that make adverse environmental contributions, such as an assessment of those who are significantly contributing to greenhouse gases, ozone depletion, and global warming, by way of non-limiting example.

In accordance with the foregoing, the disclosure of a mobile air quality monitor may include a personal, portable stand-alone monitor, such as may be associated with a wristband, a necklace, a hair band, a sweat band, or an article of clothing, by way of non-limiting example; and may include a mobile monitor that may be an integrated aspect of another device, such integration with a watch, a computer, a mobile communications device, an automobile, or a piece of wearable equipment, by way of non-limiting example. Mobile equipment integrating the mobile air quality monitor of the embodiments may include equipment used in industries particularly susceptible to injurious air quality, such as helmets used in mining applications, mobile or wearable equipment in laboratories, movable equipment in a doctor's office, or the like. Thus, the embodiments of a monitor may serve to be or be part of products dedicated to improving lifestyle, recreation, healthcare, mining and high-risk industries, research laboratories, automotive industry, tourism, and the like.

Figure 1B:
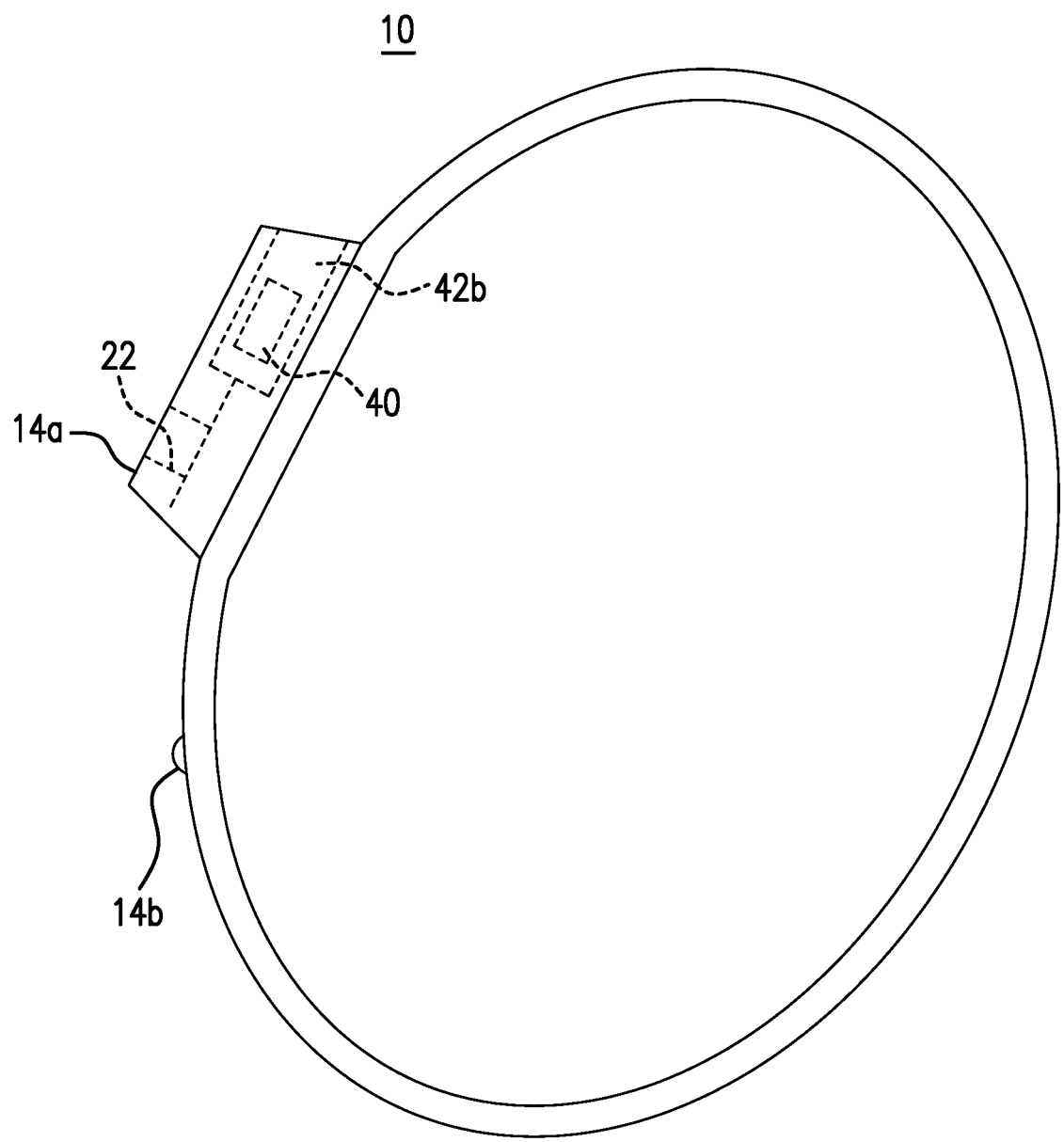
FIG. 1B is a diagram illustrating an embodiment of a personal, portable air quality monitor.
Figure 1C:
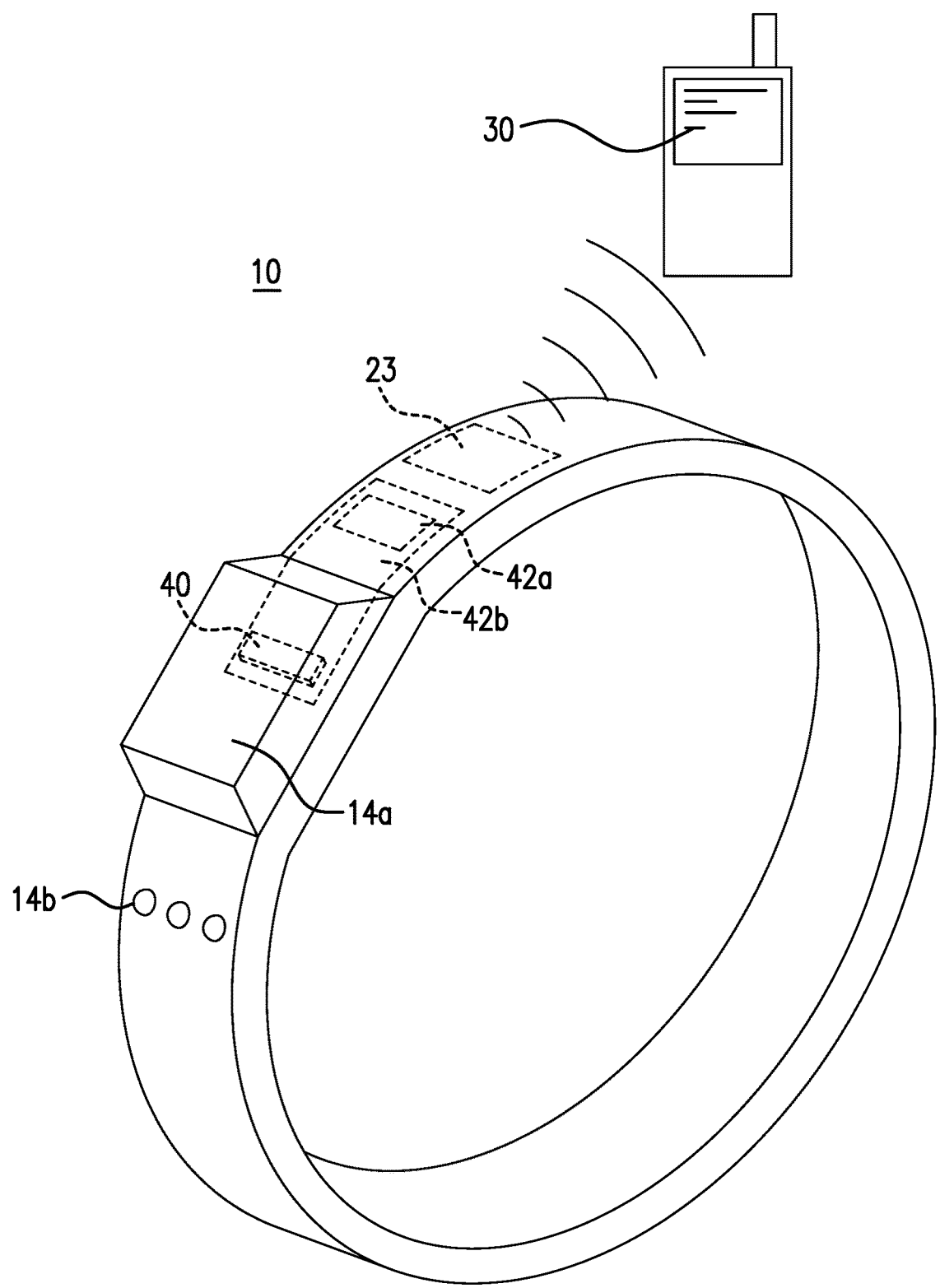
FIG. 1C is a diagram illustrating an embodiment of a personal, portable air quality monitor.

In light of the foregoing, discussed herein is a personal, portable air quality monitor. More specifically, FIGS. 1A, 1B and 1C respectively illustrate a front, side and profile view of a personal, portable monitor 10, illustrated in the form of standalone bracelet, such as may be formed by injection molding or other known methods, and which may structurally comprise plastics, polymers, polycarbonate, rubber, metal, silicone, neoprene, fabrics, or the like. The exemplary monitor 10 may be for use by an individual to monitor air quality for air in the vicinity of the individual. Of note, the bracelet shown in FIG. 1 is provided only by way of example, and is non-limiting as to the disclosed embodiments of a personal, portable air quality monitor.

In embodiments of FIG. 1, the monitor 10 may include a complex user interface 14a, such as a small display screen, to present sensed air data and/or notifications 16 to the user, and/or may include one or more simplistic user interfaces 14b, such as multiple colors of LEDs indicative of levels of air contaminants in the immediate environment, to present air quality data to the user.

A first tier communications system 22 may be provided between sensors of air quality 40 and the user interfaces 14a, 14b, to allow for this communication of air quality to the user. Of note, the first tier communication system 22 may carry the information from sensors 40 to a user interface 14a, 14b not physically associated with the device including sensors 40, as discussed further herein below. The first tier communications system 22 may include hard wiring, Bluetooth, near field communication, wifi or internet of things (IoT) connectivity, by way of non-limiting example, and may, of course, include processing of the sensor data before the data is provided to the under interface 14a, 14b.

Further, the monitor 10 may include a second tier communication system 23 to, in additional and alternative embodiments, allow for sharing of the data incurred by the monitor 10 outside of the immediate vicinity 24 of the monitor, such as to the cloud (not shown). Of note, the second tier communication system 23 may send the information to a physical location remote from sensors 40, and may also not be physically associated with the device including sensors 40, as discussed further herein below. The second tier communication system 23 may include hard wiring, Bluetooth, near field communication, wifi or internet of things (IoT) connectivity, GPS, cellular communications capability, or the like, by way of example, and may additionally include processing of the sensor data prior to the remote communication of the data.

In some embodiments, the communication system tiers 22, 23 may be combinations of the same, different, local, or remote communications systems, such as wherein a smartphone app 30 provides, on the smartphone display 14a, indications to the user of air quality and notifications upon receipt of same from the sensors 40 of monitor 10, such as wherein the monitor 10 is worn by the user but communicates via the first communication tier 22 with the smartphone app. Then, in turn and by way of non-limiting example, the smartphone may display the received information on display 14a.

Further, the smartphone may communicate the received information to the cloud, thus acting as communications tier 23. That is, the smartphone's cellular or wife capabilities may serve as the second tier communication system 23. Accordingly, the monitor 10 may effectively "use" the smartphone's communication capabilities to communicate its incurred data remotely, such as to the cloud, for provision to other users, as discussed further herein.

Needless to say, in some embodiments similar to those discussed immediately herein above, an independent user interface on the monitor 10 itself may be unnecessary. Or, the monitor 10 may include only a simple interface 14b, such as one or more LED's, to indicate to the user that the user should view her smartphone app on smartphone display 14a for a more informative indication related to air quality.

The air quality monitor 10 thus may include one or more air quality aspect sensors 40, and at least one air access point 42a for those sensors 40. That is, the sensors 40 that make the air quality assessment in the monitor must have access to air in the localized area through an access point 42a, i.e., the sensor is not hermetically sealed within the monitor 10. The access point(s) 42a may have associated therewith an access chamber or chambers 42b that internally serve(s) the air received through access point 42a to the sensors within the monitor 10. The access point chamber 42b may preferably be small in size so as to minimize the form factor of monitor 10. For example, the access point chamber 42b may be on the order of millimeters to ½ inch in size, and may accommodate the sensors and/or sensor board, and the requisite clearance for the same, therein.

Further, the air entering access point 42a or chamber 42b may be forced air or natural air. As such, access point 42a may have associated therewith one or more fans or blowers (not shown), or air may enter naturally through access point 42a, such as due to air currents or user movements, by way of non-limiting example.

Sensor types for sensors 40 may include any of a variety of partially, substantially or fully miniaturized sensors, such as: printed gas sensors—including polymer printed technologies; substrate level sensors; MEMS and MOS sensors; temperature or pressure sensors; integrated circuit sensors; electrochemical or printed electrochemical sensors; chemiresistive sensors; optical sensors; humidity sensors; and the like. The sensor types may sense any of the various factors that make up air quality, such as those factors discussed throughout.

Sensors 40 may each operate continuously or non-continuously, or may vary between continuous or non-continuous operation. For non-continuous operation, a clock (not shown) may indicate the timing of the sensing operation. The timing of the sensing for each sensor may vary, such as in accordance with the danger level of that which is sensed, by way of non-limiting example. For example, carbon monoxide may be sensed at more regular intervals than is ozone.

The disclosed monitor 10 may vary as to its productive life time without departing from the spirit or scope of the disclosure. That is, the individual monitor 10 may be intended for longer term use or limited term use. For example, a limited term use monitor 10 may be disposable to enable use in, for example, high risk environments such as in a mining helmet, or to enable use in temporary environments, such as in a wristband for use in a theme park. As such, the power requirements of the device may be met in a variety of ways as will be understood by the skilled artisan in light of the discussion herein, such as using a battery, a rechargeable battery, a solar-rechargeable battery, wired or wireless charging, solar charging, or the like.

Figure 2A:
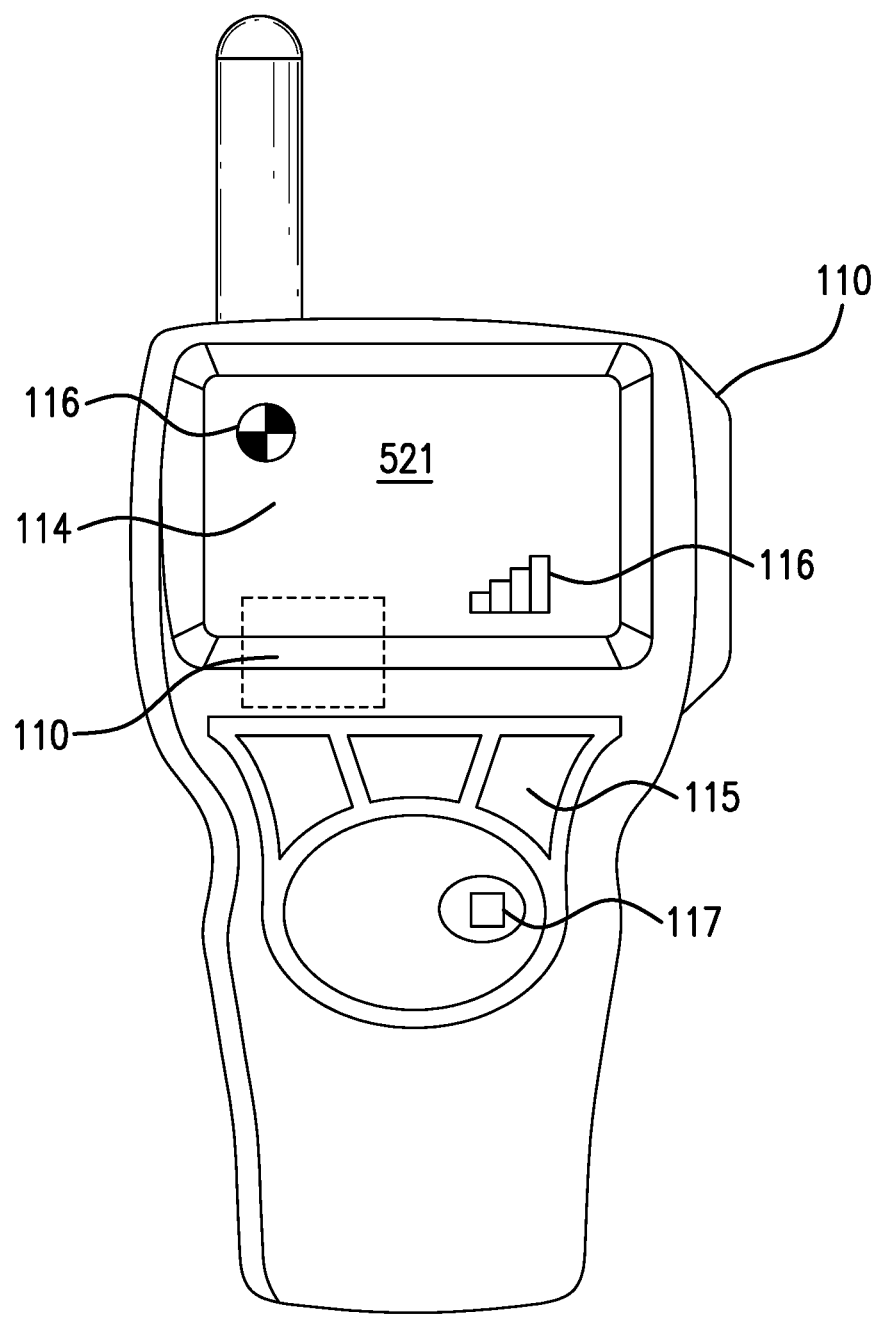
FIG. 2A is a diagram illustrating an embodiment integrating a portable, personal air quality monitor into a mobile device.
Figure 2B:
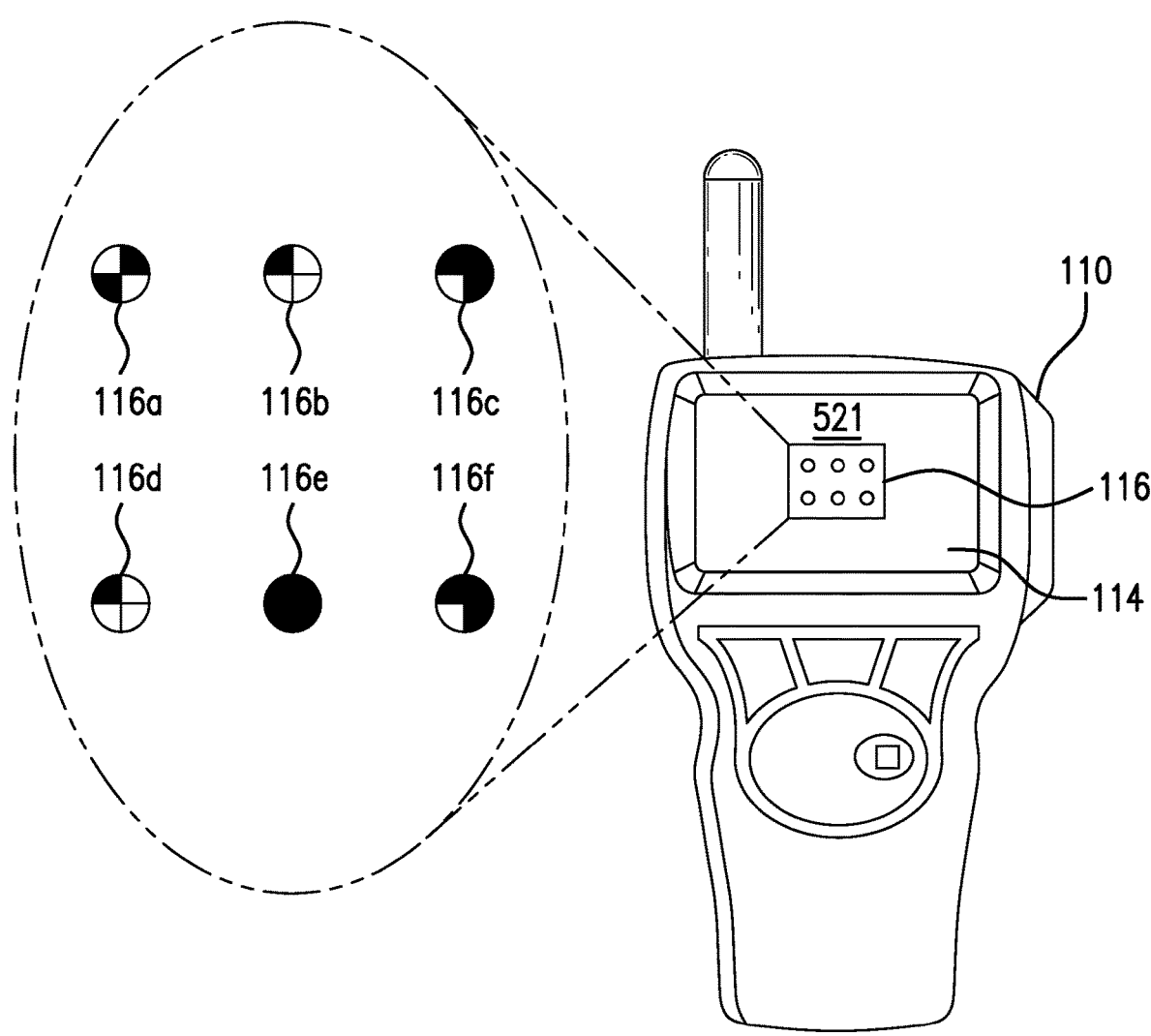
FIG. 2B is a diagram illustrating an embodiment of a user interface of a portable, personal air quality monitor integrated into a mobile device.

With reference to FIG. 2A, illustrated is the inclusion of an air quality monitor 10 within a mobile device 110. The exemplary device illustrated in FIG. 2 is a "walkie-talkie", although the skilled artisan will appreciate that this illustration is exemplary in nature only, and that any portable device may include an integrated embodiment of the disclosed air quality monitor. By way of non-limiting example, the air quality monitor may be integrated with a smartphone, a watch, an employee badge, a belt buckle, a smartphone cover or similar cover for a mobile device, a shoe, or the like. Moreover, although the illustrated device may communicate over short distances using radio frequencies, such as in a high risk mining environment in the manner of a walkie talkie, or with a closely-coupled device, such as a smartphone, the disclosed embodiments may also be operable with devices that use any type of communication methodologies. Accordingly, the monitor may be equipped to communicate, with local and/or remote devices, using any type of known communication method, such as Bluetooth, RF, NFC, cellular, wifi, IOT protocols, or the like, as discussed throughout.

In the illustration of FIG. 2A, air quality monitor data 112 may be provided to the user over the same user interface 114 as is otherwise used by the device 110, or may be communicated to the user via an additional or alternative user interface. For example, a typical user interface 114 for a walkie talkie may include a display, such as on a liquid crystal display (LCD) or LED or OLED display, of available power levels, signal strength, and/or activity of communications, and in the disclosed embodiments the user interface 114 may additionally include: one or more buttons to receive user input or commands 115; a simple or complex display of air quality 116, such as a number of bars indicative of air quality; and/or one or more LED's 117 on the walkie talkie, such as may indicate to the user that the user should check his or her mobile device app for air quality information (as discussed above, by way of example, with respect to FIG. 1).

A user interface for air quality monitoring may include different indications for different aspects of air quality. For example, aspects of air quality of particular interest in a given environment or to a particular individual may be monitored with particularity, and the choice of such particular elements of air quality may or may not be subjected to choice by and/or display or indication to the user. For example, in the illustration of FIG. 2B, the air quality aspect 116 of the user interface 114 may comprise six circles 116a, 116*b*, 116*c*, 116*d*, 116*e*, 116*f*, each having four "pie slices" per circle, to indicate factors of air quality.

In the illustrated embodiment, four pie slices in a given circle may indicate optimal air quality for that factor of air quality. Exemplary air quality factors may include $CO_2$ levels, particulate levels, pollen levels, UV levels, mold levels, and dust levels. Other air quality aspects which may be monitored include, but are not limited to, CO, NO2, SO2, O3, particle pollution PM 2.5, particle pollution PM 10, or lead (Pb), by way of non-limiting example. As such, it goes without saying that sensors 40 associated with each of the air quality factors to be monitored would be included in the mobile air quality monitor 10, should have access to the air in that particular environment via air access point 42*a*, and should have sufficient connectivity to be able to communicate sensor data via first communication tier 22 to the understandable user interface 114.

Thereby, a user may be informed, in-situ, as to the particular air quality factor or factors important to that person. Those factors may be selectable to the person, or may be preset for monitor 10. Thus, for example, if an individual suffers from severe asthma, an alert of a high pollen particulate count may indicate to that person that she should leave the vicinity immediately. These selections may be based on user wants or needs that are input from user, such as to the user interface, such as during initial setup or during discrete operation timeframes.

Figure 3:
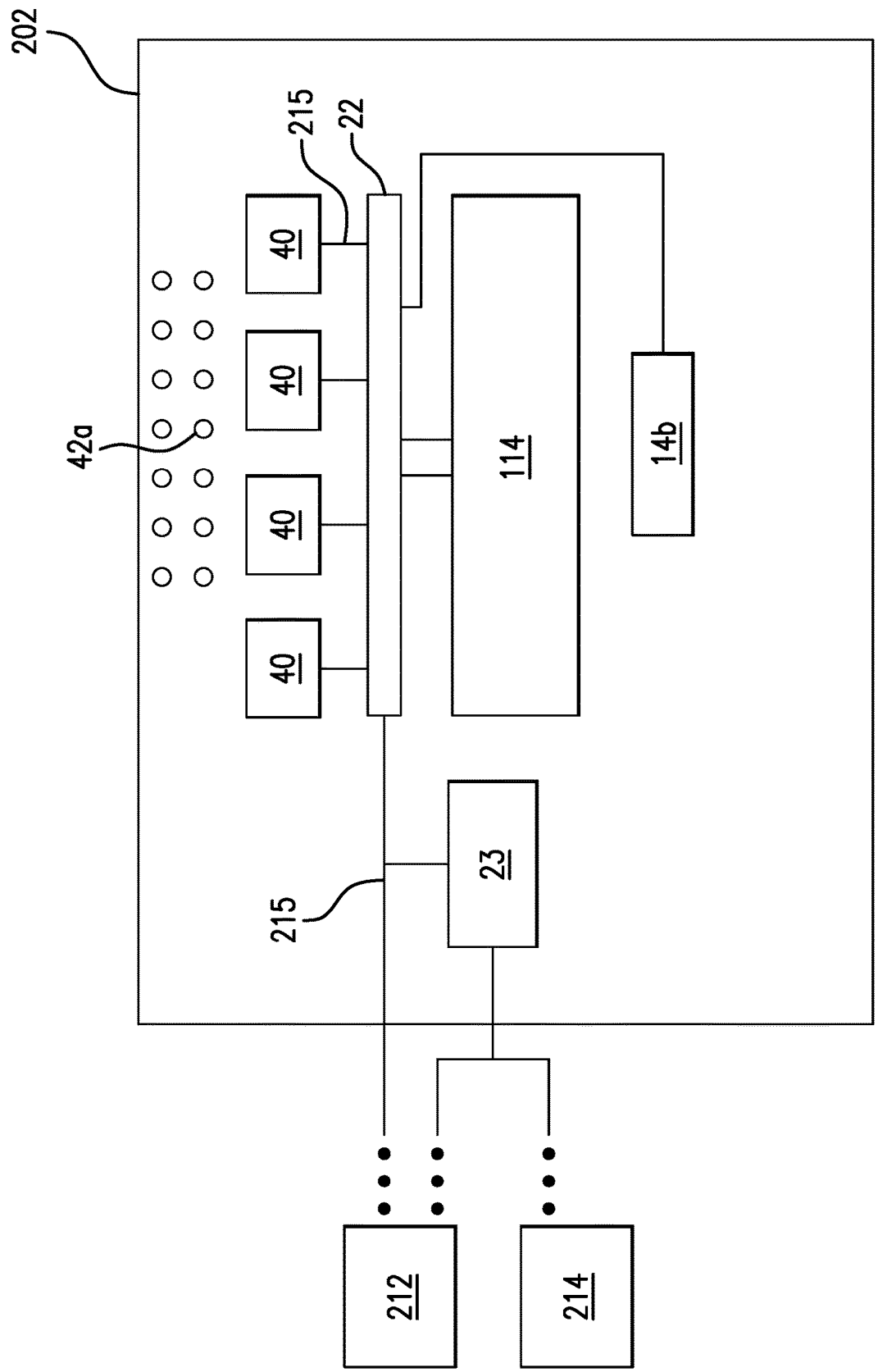
FIG. 3 is a diagram illustrating an embodiment of the connectivity of a portable, personal air quality monitor.

FIG. 3 illustrates the connection of the sensors 40 to the user interface 114, optionally to an external communication interface (such as a nearby smartphone) 212, and, optionally, to the cloud or another remote location 214 via communication means 23, such as to enable sharing of incurred data 215. In the embodiment of FIG. 3, the mobile air quality monitor 202 may be equipped with a plurality of sensors 40 capable of monitoring a number of air quality factors, such as six factors in the example herein above. Through the user interface 114, the user may be provided with the capability to access the data from all, or only select or selected ones, of these sensors 40.

The data from the sensors 40 may be communicated to the user interface 114 via communication first tier 22 using any of the communication methodologies discussed herein or others known to the art, such as, by way of non-limiting example, RF, hardwire, Bluetooth, wifi, cellular, or the like. Prior to presentation on the user interface 114, the data may be stored in one or more computing memories, such as in a database format, and may be time buffered as necessary prior to presentation on the user interface, as discussed further herein below in relation to FIG. 4. Presentation on the user interface 114 may preferably occur pursuant to an indication to make such a display from one or more computing processors associated with the user interface 114 and/or the sensors 40, as also discussed further herein below in relation to FIG. 4.

Communication of user input to the user interface 114 may or may not occur in the same manner as discussed herein with respect to communication from the sensors to the user interface, as will be understood by the skilled artisan in light of the discussion herein. That is to say, the user interface 14*a*, 14*b*, 114 connectivity first tier communication system 22 may or may not be bidirectional.

Figure 5:
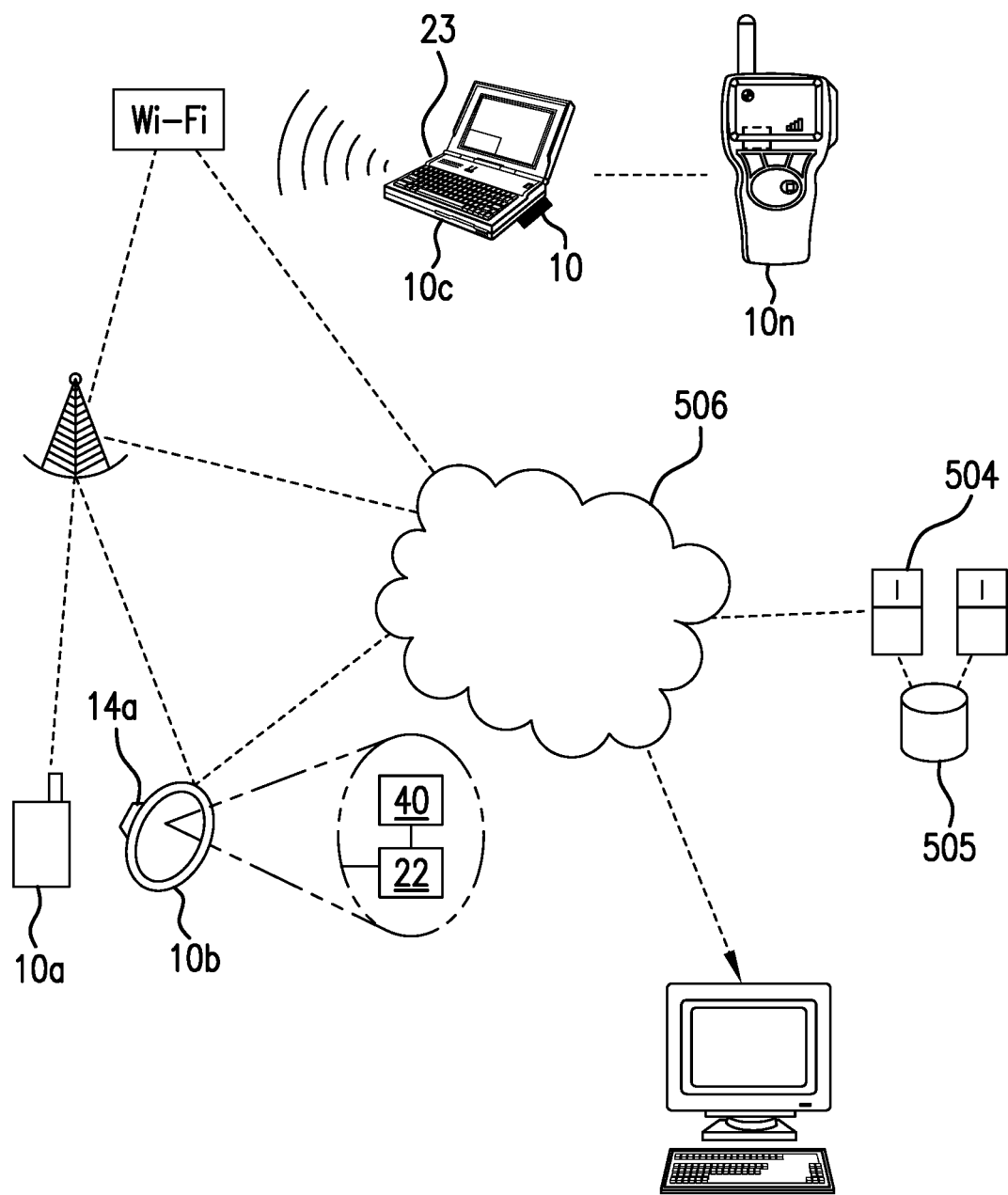
FIG. 5 is a diagram of an embodiment of a system employing multiple portable, personal airy quality monitors.

Yet further, and with or without direction from the user as input to the user interface 114, one or more second tier communication methodologies 23 may allow for communication of the sensor data to the cloud, such as to allow for sharing with other users in different environments, or in the same environment, as is also discussed further in relation to FIG. 5. That is, the air quality monitor 10 may be capable of communicating 23, such as via RF, Bluetooth, NFC, or cellular communications, the incurred data in relation to air quality, and/or any alerts or notifications associated therewith, to a remote location, such as to the cloud, for storage, such as in a database, for access at a later time by the user of that sensor, and/or for access by other users.

The communication from the monitor to the cloud may or may not occur using the same communication methodology as the communication from the monitor to the local user interface or interfaces, i.e., the first and second tier communications 22, 23, may use the same or substantially the same hardware. Moreover, communications may occur serially through the first and second tiers 22, 23, such as from the sensors 40 to the user interface 14*a*, 14*b*, 114, and then from a processing system associated with the user interface 14*a*, 14*b*, 114 (such as the processing system of a smartphone proximate to the monitor 10) to the cloud.

Whether or not the first and second tier communication systems 22, 23 overlap or are distinct, the eventual presence of in-situ data at a remote storage site, such as in the cloud, may allow for remote users to make decisions about an environment in which they are not then-present. For example, a parent of a child with a medical condition may be able to review air quality in an amusement park, and may thus be enabled to avoid starting a trip to that amusement park if the cloud data from in-situ monitors 10 at the amusement park indicates that the air quality would exacerbate the child's condition.

Figure 4:
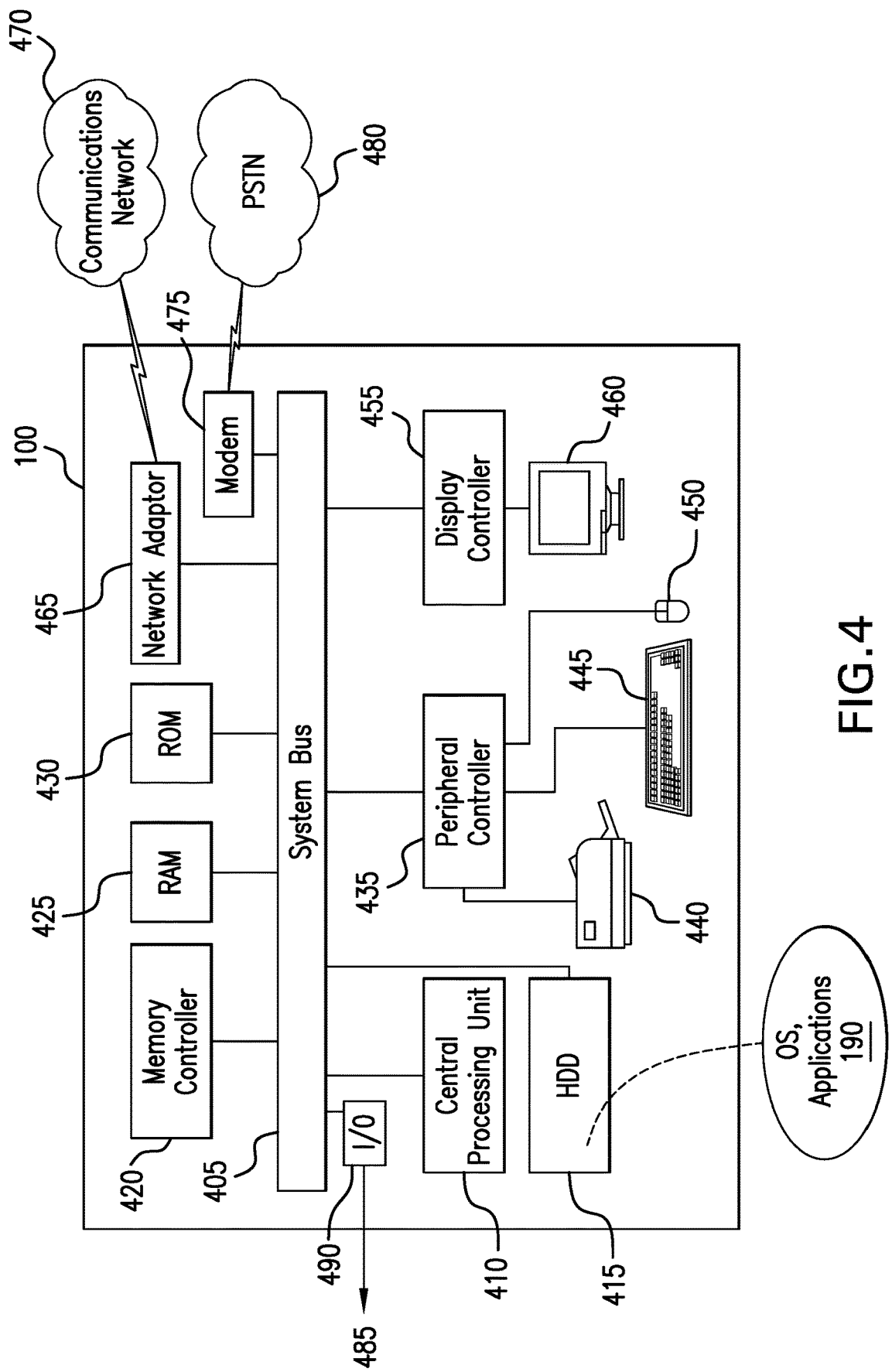
FIG. 4 is a schematic block diagram illustrating a computing system in an embodiment.

FIG. 4 illustrates an embodiment of a computer processing system 400 that may receive monitor data and other inputs, such as user inputs, as discussed herein, and that may perform the processing, logic, and communications control discussed throughout. That is, the computing system 400 may be used in accordance with herein described monitor 10, systems and methods.

Computing system 400 is capable of executing software, such as an operating system (OS) and one or more computing applications 490. The software may likewise be suitable for operating hardware, such as via inputs/outputs (I/O), using said applications 490.

The operation of computing system 400 is controlled primarily by computer readable instructions, such as instructions stored in a computer readable storage medium, such on a hard disk drive (HDD) 415, RAM, ROM, EEPROM, or the like (not shown). Such instructions may be executed within central processing unit (CPU) 410 to cause computing system 400 to perform the disclosed operations. In many known computer servers, workstations, PLCs, personal computers, mobile devices, and the like, CPU 410 is implemented in an integrated circuit called a processor.

The various illustrative logics, logical blocks, modules, alerts and assessments described in connection with the embodiments disclosed herein may be implemented or performed with any of a general purpose CPU, a digital signal processor (DSP), an application specific integrated circuit (ASIC), a field programmable gate array (FPGA) or other programmable logic device, discrete gate or transistor logic, discrete hardware components, or any combination thereof, respectively acting as CPU 410. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It is appreciated that, although computing system 400 is shown to comprise a single CPU 410, such description is merely illustrative, as computing system 400 may comprise a plurality of CPUs 410, which may be distributed on and off of monitor 10. Additionally, the computing system 400 may exploit the resources of remote or parallel CPUs (not shown), for example, through local or remote communications network 470 or some other data communications means.

In operation, CPU 410 fetches, decodes, and executes instructions from a computer readable storage medium, such as HDD 415. Such instructions can be included in the software, such as the operating system (OS), machine code, executable programs/applications, and the like. Information, such as computer instructions and other computer readable data, is transferred between components of computing system 400 via the system's main data-transfer path. The main data-transfer path may use a system bus architecture 405, although other computer architectures (not shown) can be used.

System bus 405 may include data lines for sending data, address lines for sending addresses, and control lines for sending interrupts and for operating the system bus. Some busses provide bus arbitration that regulates access to the bus by extension cards, controllers, and CPU 410.

Memory devices coupled to system bus 405 can include random access memory (RAM) 425 and read only memory (ROM) 430. Such memories include circuitry that allows information to be stored and retrieved. ROMs 430 generally contain stored data that cannot be modified. Data stored in RAM 425 can generally be read or changed by CPU 410 or other communicative hardware devices. Access to RAM 425 and/or ROM 430 may be controlled by memory controller 420. Memory controller 420 may provide an address translation function that translates virtual addresses into physical addresses as instructions are executed.

The steps and/or actions described in connection with the aspects disclosed herein may be embodied directly in hardware, in a software module executed by a processor, or in a combination of the two, in communication with memory controller 420 in order to gain the requisite performance instructions. That is, the described software modules to perform the functions and provide the directions discussed herein throughout may reside in RAM memory, flash memory, ROM memory, EPROM memory, EEPROM memory, registers, a hard disk, a removable disk, a CD-ROM, or any other form of storage medium known in the art. Any one or more of these storage medium may be coupled to the processor 410, such that the processor can read information from, and write information to, that storage medium. In the alternative, the storage medium may be integral to the processor. Further, in some aspects, the processor and the storage medium may reside in an ASIC. Additionally, in some aspects, the steps and/or actions may reside as one or any combination or set of instructions on an external machine readable medium and/or computer readable medium as may be integrated through I/O port(s) 485, which may include wireless ports.

In addition, computing system 400 may contain peripheral controller 435 responsible for communicating instructions using a peripheral bus from CPU 410 to peripherals and other hardware, such as printer 440, keyboard 445, and mouse 450. An example of a peripheral bus is the Peripheral Component Interconnect (PCI) bus.

One or more hardware input/output (I/O) devices 485, such as sensors 40, may be in communication with hardware controller 490. This hardware communication and control may be implemented in a variety of ways and may include one or more computer busses and/or bridges and/or routers. The I/O devices controlled may include any type of port-based (including wireless "ports") hardware, and may additionally comprise software, firmware, or the like, such as the disclosed sensors inputs/outputs 40, and can also include network adapters and/or mass storage devices from which the computer system 400 can send and receive data for the purposes disclosed herein. The computer system 400 may thus be in communication with the Internet/cloud or other networked devices/PLCs via the I/O devices 485 and/or via communications network 470.

Display 460, which is controlled by display controller 455, may optionally be used to display visual output generated by computing system 400, and may comprise, for example, display 14a. Display controller 455 may also control, or otherwise be communicative with, the display. Visual output may include text, graphics, animated graphics, and/or video, for example. Display 460 may be implemented with a CRT-based video display, an LCD-based display, gas plasma-based display, touch-panel, or the like.

Further, computing system 400 may contain network adapter 465 which may be used to couple computing system 400 to external devices or an external communication network 470, which may include or provide access to the Internet, and hence which may provide cloud access to the air quality data discussed herein as the second tier communication system 23. Communications network 470 may provide user access to computing system 400 with means of communicating and transferring software and information electronically, and may be coupled directly or indirectly to computing system 400. It is appreciated that the network connections shown are exemplary, and other means of establishing communications links between multiple computing systems 400, and/or with remote users, may be used.

It is appreciated that computing system 400 is merely illustrative of a computing environment in which the herein described systems and methods may operate, and thus does not limit the implementation of the herein described systems and methods in computing environments having differing components and configurations. That is, the inventive concepts described herein may be implemented in various computing environments using various components and configurations.

FIG. 5 illustrates a system incorporating multiple air quality monitors 10a, 10b, 10c, . . . 10n. In the illustration, several air quality monitors, each in different environments and each comprising standalone, integrated, portable air quality monitors, receive individual sensor data via a first communications tier 22, and communicate data from each such air quality monitor 10a, 10b, 10c, . . . 10n to one or more servers 504, such as may be resident in or associated with the cloud 506, to allow for storage of this data in one or more databases associated with the servers 504. The communication of this data may occur, by way of non-limiting example and as illustrated, over the second tier system 23 in the form of a cellular network, a Bluetooth network, a wired network, or combinations thereof, by way of non-limiting example. Once stored at the server database 505, this data may be made available, such as in a searchable format based on entry of a geographic location, from the cloud 506, as illustrated.

Figure 6:
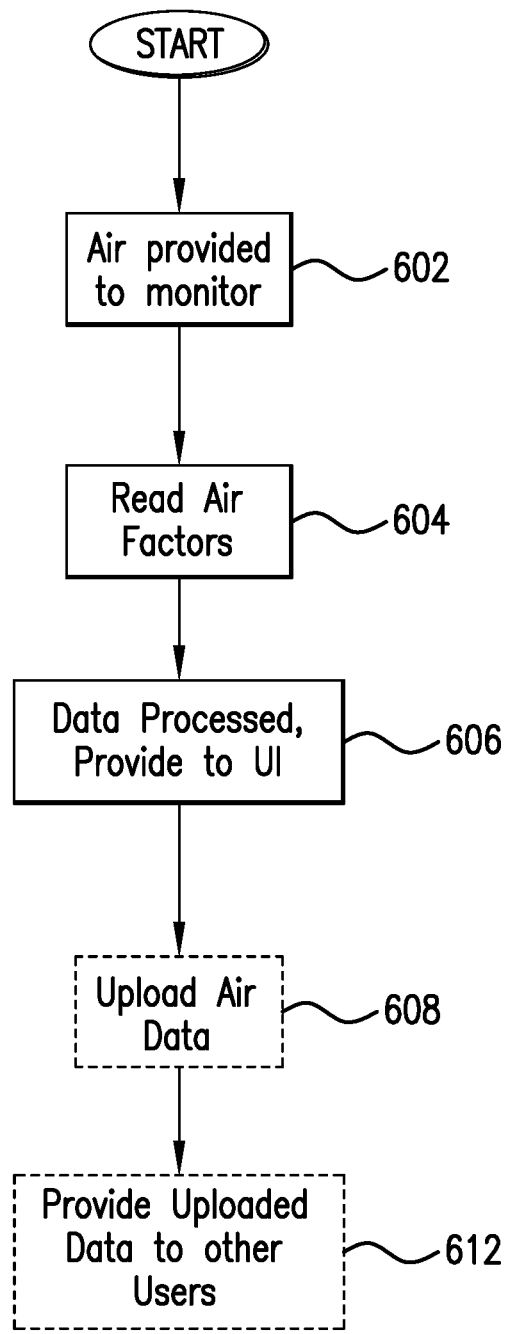
FIG. 6 is a flow diagram illustrating a method of monitoring air quality in accordance with an embodiment.

FIG. 6 is a flow diagram illustrating a method 600 related to the disclosed embodiments. In the illustration, at step 602 air is provided to one or more air quality factor sensors of a personal, portable air quality monitor. At step 604, each of the one or more sensors reads the factor relevant to that sensor. This data is provided, via one or more processors, to a user interface at step 606. As discussed herein, the user interface may preferably be associated with one or more mobile devices.

At optional step 608, the data provided to the user interface, and any additional data deemed suitable for upload, is uploaded over one or more networks to the cloud. This accumulated data over multiple locations may then be made available by the aforementioned user interface, or over other secondary user interfaces, to multiple other users at step 612.

Data safety and security for uploads/downloads may be managed using cellular, networking, and/or IP protocols. For example, cellular security and encryption protocols for mobile devices may be used to maintain user confidentiality during the data exchanges of steps 608 and 612.

Moreover, aspects of a method executed in accordance with the disclosure may, as will be understood by the skilled artisan, include the execution of software, such as using the computing system indicated in FIG. 4. In order to perform that aspects discussed herein, such software may include engines, subroutines, or the like to performed the disclosed functionality, including evaluation of current air quality data and historical air quality data, including enablement of user interaction with such data, such as via the user interface(s) discussed herein; GPS or similar geo-location of the air quality monitor and/or geo-coding of the data associated therewith; profile settings, such as user preferences; indoor versus outdoor indications or settings; external input to enable analysis for or providing of air quality data to a user, such as external input from weather stations, other user, or the like; and other analytics or network communications suitable for use in the disclosed embodiments.

Figure 7:
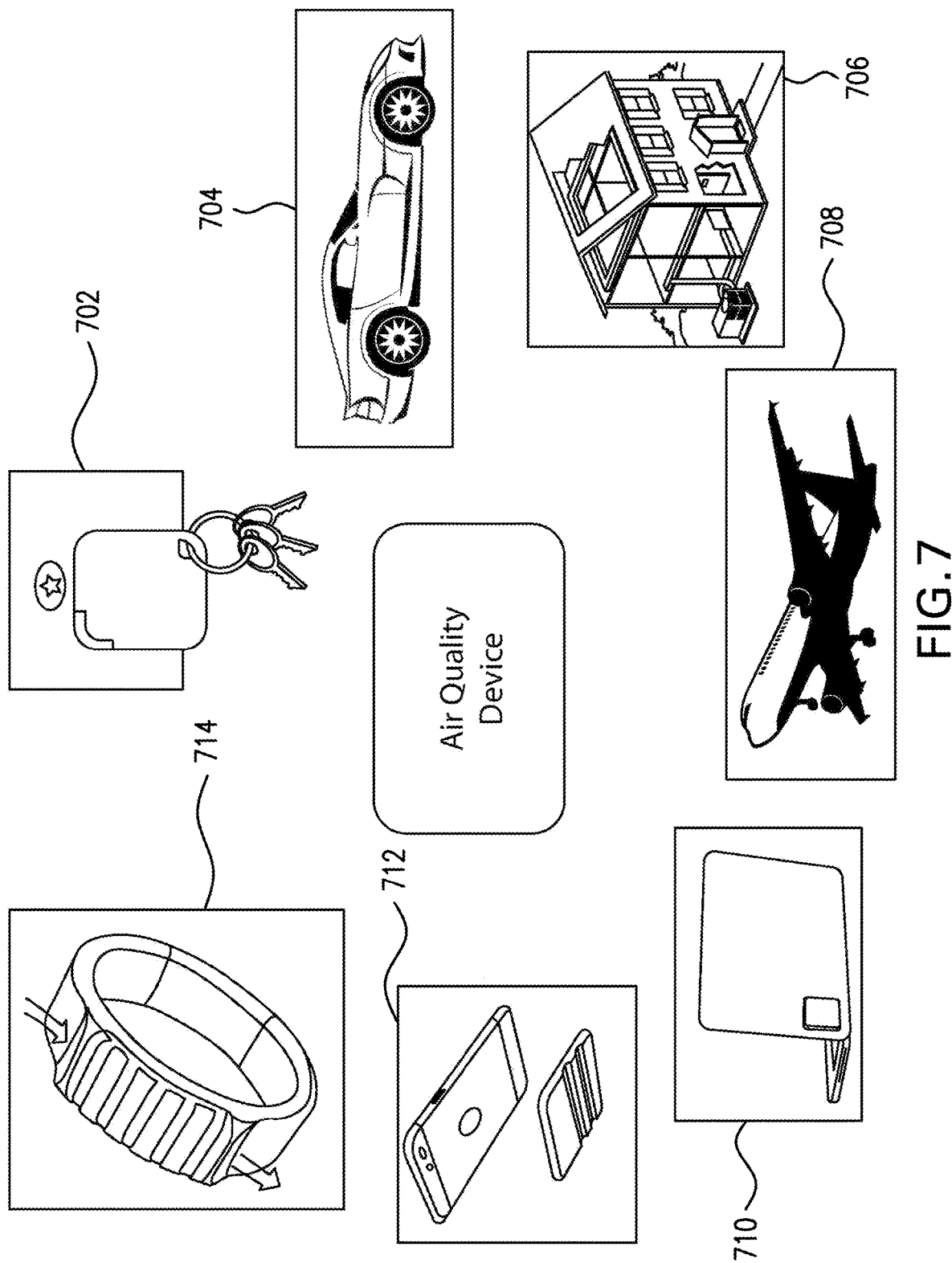
FIG. 7 is an environmental optionality illustration for a portable, personal air quality monitor.

Thus, disclosed is a personal, portable air quality monitor. The monitor 10 may be independent, or may be associated with a variety of secondary devices in a variety of sensing environments, such as environments 702, 704, 706, 708, 710, 712, 714. This is illustrated by way of example in the environmental illustration of FIG. 7, although it will be appreciated that the disclosure is not limited to the environments and/or the devices associated with monitor 10 in FIG. 7.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A personal air quality monitor, comprising:
   a wearable housing suitable for physical association with a person;
   an air inlet capable of providing air flow from an environment outside the wearable housing to at least one chamber within the housing;
   a plurality of sensors resident within the at least one chamber, suitable for receiving the airflow and measuring air quality factors of the environment as associated with the airflow;
   a first communication processing system suitable for processing the air quality factor measurements comprised of at least levels of CO, CO2, NO2, O3 and particulates, and communicating the processed air quality factor measurements to a local user interface cognizable to the person; and
   a remote processing system that is non-local to the local user interface and which receives the air quality factor measures wirelessly from the first communication processing system, and which processes the received air quality factor measurements for display on a remote user interface of a type different than the local user interface.

2. The monitor of claim 1, wherein the wearable housing at least partially forms a bracelet.

3. The monitor of claim 1, wherein the physical association comprises integration with a garment.

4. The monitor of claim 1, wherein the wearable housing is integrated with a mobile communications device.

5. The monitor of claim 1, wherein the wearable housing is comprised of at least one selected from the group consisting of plastics, polymers, polycarbonate, rubber, metal, silicone, neoprene, and fabrics.

6. The monitor of claim 1, wherein the local user interface comprises a display screen.

7. The monitor of claim 1, wherein the local user interface comprises at least one light emitting diode.

8. The monitor of claim 1, wherein the local user interface comprises alerts regarding the processed air quality factor measurements.

9. The monitor of claim 8, wherein at least one of the alerts refers the person to view a secondary device's user interface.

10. The monitor of claim 1, wherein the first communication system comprises at least one of hard wiring, Bluetooth, near field communication, wifi and internet of things (IoT) connectivity.

11. The monitor of claim 1, wherein the sensors comprise partially, substantially or fully miniaturized sensors.

12. The monitor of claim 1, wherein the sensors comprise at least one selected from the group consisting of printed gas sensors, substrate level sensors, MEMS and MOS sensors, temperature sensors, pressure sensors, integrated circuit sensors, electrochemical sensors, printed electrochemical sensors, humidity sensors, chemiresistive sensors, and optical sensors.

13. The monitor of claim 1, wherein at least ones of the sensors comprise noncontinuously operating sensors.

14. The monitor of claim 1, wherein the wearable housing comprises a disposable housing and a power source.

* * * * *